(12) United States Patent
Ni et al.

(10) Patent No.: US 9,708,240 B2
(45) Date of Patent: Jul. 18, 2017

(54) METHOD FOR PREPARING POLYOXYMETHYLENE DIMETHYL ETHER CARBONYL COMPOUND AND METHYL METHOXYACETATE

(71) Applicant: DALIAN INSTITUTE OF CHEMICAL PHYSICS, CHINESE ACADEMY OF SCIENCES, Dalian (CN)

(72) Inventors: Youming Ni, Dalian (CN); Wenliang Zhu, Dalian (CN); Hongchao Liu, Dalian (CN); Yong Liu, Dalian (CN); Zhongmin Liu, Dalian (CN); Shuanghe Meng, Dalian (CN); Lina Li, Dalian (CN); Shiping Liu, Dalian (CN); Hui Zhou, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 0 days.

(21) Appl. No.: 15/105,364

(22) PCT Filed: Dec. 23, 2013

(86) PCT No.: PCT/CN2013/090242
§ 371 (c)(1),
(2) Date: Jun. 16, 2016

(87) PCT Pub. No.: WO2015/096009
PCT Pub. Date: Jul. 2, 2015

(65) Prior Publication Data
US 2017/0001941 A1    Jan. 5, 2017

(51) Int. Cl.
*C07C 67/37* (2006.01)
*C07C 67/38* (2006.01)
*C07C 69/708* (2006.01)

(52) U.S. Cl.
CPC .............. *C07C 67/37* (2013.01); *C07C 67/38* (2013.01)

(58) Field of Classification Search
None
See application file for complete search history.

(56) References Cited

U.S. PATENT DOCUMENTS 2,273,269 A * 2/1942 Johnson ................. C07C 67/37
560/187
2011/0319654 A1* 12/2011 Hazel ..................... C07C 67/37
560/232

FOREIGN PATENT DOCUMENTS

| CN | 103172516 A  | 6/2013 |
| EP | 0088529 A2   | 9/1983 |
| JP | S5846035 A   | 3/1983 |
| JP | H06228045 A  | 8/1994 |
| WO | 2010048300 A1 | 4/2010 |

OTHER PUBLICATIONS

Machine generated English language translation of CN 103172516, Jun. 26, 2013, p. 1-14.*
F.E. Celik et al., Angew. Chem. Int. Ed. 48 (2009), 4813-4815.
F.E. Celik et al., Journal of Catalysis 270 (2010), 185-195.
F.E. Celik et al., Journal of Catalysis 274 (2010), 150-162.

* cited by examiner

*Primary Examiner* — Jafar Parsa
*Assistant Examiner* — Amy C Bonaparte
(74) *Attorney, Agent, or Firm* — Enshan Hong; VLP Law Group LLP

(57) ABSTRACT

A method for preparing a polyoxymethylene dimethyl ether carbonyl compound and/or methyl methoxyacetate as intermediates for producing ethylene glycol, which comprises passing a raw material: polyoxymethylene dimethyl ether or methylal together with carbon monoxide and hydrogen gas through a reactor carrying an acidic molecular sieve catalyst, and performing a reaction to prepare a corresponding product under an appropriate condition where no other solvent is added, in which the process of the reaction is a gas-liquid-solid three-phase reaction, the raw material of polyoxymethylene dimethyl ether or methylal has a high conversion rate, each product has a high selectivity, the catalyst has a long service life, additional solvents are not required to be used, and reaction conditions are relatively mild.

11 Claims, No Drawings

METHOD FOR PREPARING POLYOXYMETHYLENE DIMETHYL ETHER CARBONYL COMPOUND AND METHYL METHOXYACETATE

RELATED APPLICATIONS

This is a U.S. national stage of international application No. PCT/CN2013/090242 filed on Dec. 23, 2013.

TECHNICAL FIELD

This invention relates to a method for preparing a polyoxymethylene dimethyl ether carbonyl compound and methyl methoxyacetate as intermediates for producing ethylene glycol.

BACKGROUND ART

Ethylene glycol is an important chemical raw material and strategic material in China, which is used for producing polyester, which may be further used for producing terylene, PET bottles, and thin films, explosives, and glyoxal, and may be used as an antifreeze agent, a plasticizer, a hydraulic fluid, a solvent, etc. In 2009, the amount of imported ethylene glycol of China exceeded 5.80 million tons. It is predicted that the demand for ethylene glycol in China will be up to 11.20 million tons by 2015, while the throughput is about 5.00 million tons, and the gap of supply and demand is still up to 6.20 million tons. Therefore, the development and the application of new techniques for producing ethylene glycol in China have a good market prospect. In the world, ethylene from petroleum cracking is mainly used to obtain ethylene oxide by oxidation, and ethylene glycol is obtained by the hydration of ethylene oxide. In view of current situations such as the energy resource structure of "rich coal, insufficient oil, and little gas" in China, the price of crude oil running at a high level for a long term, etc., new coal chemical techniques for preparing ethylene glycol from coal can both ensure the national energy security and fully utilize coal resource in China, and are the most realistic selection for the coal chemical industry in the future.

At present, a relatively mature domestic technique is "a packaged processing technique for synthesizing oxalate by gas phase catalysis of CO and synthesizing ethylene glycol by catalytic hydrogenation of oxalate" developed by Fujian Institute of Research on the Structure, Chinese Academy of Sciences. In early December of 2009, the first set of industrialized apparatus attracting a large number of attentions in the industry in the world—the first phase construction of "project for preparing ethylene glycol from coal" by Tongliao Jinmei Chemical Corporation, Inner Mongolian, which was a project for preparing ethylene glycol from coal with an annual production of 200 thousand tons, opened up the whole process flow, and produced a qualified product of ethylene glycol. However, the economy, the environmental protection property, the energy saving property, and the further engineering scaling-up of this process flow will be restricted by the large number of processing units, the high requirement for the purity of industrial gas, the need for the use of precious metal catalyst in the process of oxidative coupling, the need for the use of nitrogen oxides which potentially pollute the environment, and the like.

Polyoxymethylene dimethyl ether (or referred to as polyoxymethylene methylal) has a molecular formula of $CH_3O(CH_2O)_nCH_3$ wherein n≥2, and is typically simply referred to as $DMM_n$ (or $PODE_n$). In the process of the preparation of polyoxymethylene dimethyl ether, the distribution of products generated is unconscionable. Methylal and $DMM_2$ are relatively high, while the selectivity of $DMM_{3-4}$, which may be used as a diesel additive, is relatively low. Therefore, byproducts in the preparation process thereof are often required to be subjected to repeated separation and further reaction, and this consumes a large amount of energy and has a bad economy. Therefore, if methylal and $DMM_2$ as byproducts can be directly processed into a product having a higher economic value, the economy of this process will be increased.

In recent years, the research team of Professor Alexis T. Bell at UC, Berkeley, U.S., proposed a new scheme, wherein methyl methoxyacetate is prepared by using a gas phase carbonylation method of methylal and ethylene glycol is then obtained by hydrogenation hydrolysis, and wherein the most important step is the reaction of gas phase carbonylation. However, the catalyst has a short service life, the raw material gas has a low concentration of methylal, neither the conversion rate of methylal nor the selectivity of methyl methoxyacetate is desirable, and there is a considerably long distance from industrialization. [Angew. Chem. Int. Ed., 2009, 48, 4813-4815; J. Catal., 2010, 270, 185-195; J. Catal., 2010, 274, 150-162; WO 2010/048300 A1].

SUMMARY OF THE INVENTION

An object of this invention is to provide a method for preparing a polyoxymethylene dimethyl ether carbonyl compound and methyl methoxyacetate as intermediates for producing ethylene glycol by carbonylation.

To this end, this invention provides a method for preparing a polyoxymethylene dimethyl ether carbonyl compound as an intermediate for producing ethylene glycol by carbonylation, characterized in that a raw material: polyoxymethylene dimethyl ether $CH_3O(CH_2O)_nCH_3$ together with carbon monoxide and hydrogen gas is passed through a reactor carrying an acidic molecular sieve catalyst, and a reaction is performed to prepare a product: a polyoxymethylene dimethyl ether carbonyl compound under conditions where the reaction temperature is 60-140° C., the reaction pressure is 2-10 MPa, the weight hourly space velocity of polyoxymethylene dimethyl ether is 0.2-10.0 $h^{-1}$, and no other solvent is added, wherein under the condition of the reaction, at least one of the raw material and the product is liquid phase, the acidic molecular sieve catalyst is solid phase, and carbon monoxide and hydrogen gas are gas phase, such that the process of the reaction is a gas-liquid-solid three-phase reaction, and the molar ratio of carbon monoxide to the raw material is 2:1-20:1 and the molar ratio of hydrogen gas to the raw material is 1:1-5:1, wherein n≥2 and is an integer.

This invention also provides a method for preparing methyl methoxyacetate and a polyoxymethylene dimethyl ether carbonyl compound as intermediates for producing ethylene glycol by carbonylation, characterized in that a raw material: methylal $CH_3O-CH_2-OCH_3$ together with carbon monoxide and hydrogen gas is passed through a reactor carrying an acidic molecular sieve catalyst, and a reaction is performed to prepare products: methyl methoxyacetate and a polyoxymethylene dimethyl ether carbonyl compound under conditions where the reaction temperature is 60-140° C., the reaction pressure is 2-10 MPa, the weight hourly space velocity of methylal is 0.2-10.0 $h^{-1}$, and no other solvent is added, wherein under the condition of the reaction, at least one of the raw material and the product is liquid phase, the acidic molecular sieve catalyst is solid phase, and carbon monoxide and hydrogen gas are gas phase, such that the process of the reaction is a gas-liquid-solid three-phase reaction, and the molar ratio of carbon monoxide to the raw material is 2:1-20:1 and the molar ratio of hydrogen gas to the raw material is 1:1-5:1.

In one preferred embodiment, the product: polyoxymethylene dimethyl ether carbonyl compound is a product having a structural unit of —O—(CO)—CH$_2$—O— or —O—CH$_2$—(CO)—O— formed by inserting one or more carbonyl groups —CO— on a structural unit of —O—CH$_2$—O— of the molecular chain of polyoxymethylene dimethyl ether CH$_3$O(CH$_2$O)$_n$CH$_3$, wherein n≥2.

In one preferred embodiment, the polyoxymethylene dimethyl ether is dioxymethylene dimethyl ether CH$_3$O(CH$_2$O)$_2$CH$_3$.

In one preferred embodiment, the polyoxymethylene dimethyl ether carbonyl compound is one or more of

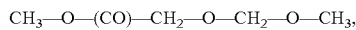

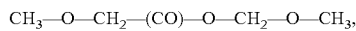

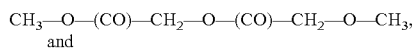
and

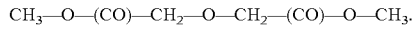

In one preferred embodiment, the structure type of the acidic molecular sieve catalyst is MWW, FER, MFI, MOR, FAU, or BEA.

In one preferred embodiment, the acidic molecular sieve catalyst is any one or a mixture of any two or more of MCM-22 molecular sieve, ferrierite, ZSM-5 molecular sieve, zeolite mordenite, Y zeolite, or Beta molecular sieve.

In one preferred embodiment, the reaction temperature is 60-120° C., the reaction pressure is 4-10 MPa, the weight hourly space velocity of the raw material is 0.5-3.0 h$^{-1}$, the molar ratio of carbon monoxide to the raw material is 2:1-15:1, and the molar ratio of hydrogen gas to the raw material is 1:1-3:1.

In one preferred embodiment, the reaction temperature is 60-90° C., the reaction pressure is 5-10 MPa, the weight hourly space velocity of the raw material is 0.5-1.5 h$^{-1}$, the molar ratio of carbon monoxide to the raw material is 2:1-10:1, and the molar ratio of hydrogen gas to the raw material is 1:1-2:1.

In one preferred embodiment, the reactor is a fixed bed reactor, a tank reactor, a moving bed reactor, or a fluidized bed reactor, which achieves continuous reaction.

In the method of this invention, the raw material: polyoxymethylene dimethyl ether or methylal has a high conversion rate, each product has a high selectivity, the catalyst has a long service life, additional solvents are not required to be used, and reaction conditions are relatively mild. The method of this invention enables continuous production and has the potential for industrial application. Also, ethylene glycol may be produced by subjecting the resultant product to hydrolysis after hydrogenation or hydrogenation after hydrolysis.

DESCRIPTION OF EMBODIMENTS

This invention provides a method for preparing a polyoxymethylene dimethyl ether carbonyl compound, characterized in that raw materials containing polyoxymethylene dimethyl ether, carbon monoxide, and hydrogen gas are passed through a reactor carrying an acidic molecular sieve catalyst, and a reaction is performed to prepare a polyoxymethylene dimethyl ether carbonyl compound under conditions where the reaction temperature is 60-140° C., the reaction pressure is 2-10 MPa, the weight hourly space velocity of polyoxymethylene dimethyl ether is 0.2-10.0 h$^{-1}$, and no other solvent is added; under the condition of the reaction, at least one of the raw material of polyoxymethylene dimethyl ether and the product of polyoxymethylene dimethyl ether carbonyl compound is liquid phase, the catalyst is solid phase, the raw materials of carbon monoxide and hydrogen gas are gas phase, and the process of the reaction is a gas-liquid-solid three-phase reaction; and in the raw materials, the molar ratio of carbon monoxide to polyoxymethylene dimethyl ether is 2:1-20:1 and the molar ratio of hydrogen gas to polyoxymethylene dimethyl ether is 1:1-5:1.

The polyoxymethylene dimethyl ether is a single component or a mixture and has a molecular formula of CH$_3$O(CH$_2$O)$_n$CH$_3$, wherein n≥2 and is an integer, and preferably, n=2, i.e., CH$_3$O(CH$_2$O)$_2$CH$_3$.

In one preferred embodiment, the process of the reaction is a gas-liquid-solid three-phase reaction, the reaction temperature is 60-120° C., the reaction pressure is 4-10 MPa, the weight hourly space velocity of the polyoxymethylene dimethyl ether is 0.5-3.0 h$^{-1}$, the molar ratio of carbon monoxide to polyoxymethylene dimethyl ether is 2:1-15:1, and the preferred molar ratio of hydrogen gas to polyoxymethylene dimethyl ether is 1:1-3:1.

In one preferred embodiment, the process of the reaction is a gas-liquid-solid three-phase reaction, the reaction temperature is 60-90° C., the reaction pressure is 5-10 MPa, the weight hourly space velocity of polyoxymethylene dimethyl ether is 0.5-1.5 h$^{-1}$, the molar ratio of carbon monoxide to polyoxymethylene dimethyl ether is 2:1-10:1, and the preferred molar ratio of hydrogen gas to polyoxymethylene dimethyl ether is 1:1-2:1.

In some embodiments of this invention, both the conversion rate of polyoxymethylene dimethyl ether and the selectivity of polyoxymethylene dimethyl ether carbonyl compound are calculated based on moles of carbons of polyoxymethylene dimethyl ether:

Conversion rate of polyoxymethylene dimethyl ether=[(moles of carbons of polyoxymethylene dimethyl ether in feed)−(moles of carbons of polyoxymethylene dimethyl ether in discharge)]÷(moles of carbons of polyoxymethylene dimethyl ether in feed)×(100%)

Selectivity of polyoxymethylene dimethyl ether carbonyl compound=(moles of carbons of polyoxymethylene dimethyl ether carbonyl compound with carbonyl groups deducted in discharge)÷[(moles of carbons of polyoxymethylene dimethyl ether in feed)−(moles of carbons of polyoxymethylene dimethyl ether in discharge]×(100%)

This invention also provides a method for preparing methyl methoxyacetate and a polyoxymethylene dimethyl ether carbonyl compound, characterized in that raw materials containing methylal CH$_3$O—CH$_2$—OCH$_3$, carbon monoxide, and hydrogen gas are passed through a reactor carrying an acidic molecular sieve catalyst, and a reaction is performed to prepare methyl methoxyacetate and a polyoxymethylene dimethyl ether carbonyl compound under conditions where the reaction temperature is 60-140° C., the reaction pressure is 2-10 MPa, the weight hourly space velocity of methylal is 0.2-10.0 h$^{-1}$, and no other solvent is added; under the condition of the reaction, at least one of the raw material of methylal and the products of methyl methoxyacetate and polyoxymethylene dimethyl ether carbonyl compound is liquid phase, the catalyst is solid phase, the raw materials of carbon monoxide and hydrogen gas are gas phase, and the process of the reaction is a gas-liquid-solid three-phase reaction; and in the raw materials, the molar ratio of carbon monoxide to methylal is 2:1-20:1 and the molar ratio of hydrogen gas to methylal is 1:1-5:1.

The structure type of the acidic molecular sieve catalyst is MWW, FER, MFI, MOR, FAU, or BEA. Preferably, the acidic molecular sieve catalyst is any one or a mixture of any two or more of MCM-22 molecular sieve, ferrierite, ZSM-5 molecular sieve, zeolite mordenite, Y zeolite, or Beta molecular sieve, and the atomic ratio of silicon to aluminum is 3:1-150:1.

In one preferred embodiment, the process of the reaction is a gas-liquid-solid three-phase reaction, the reaction temperature is 60-120° C., the reaction pressure is 4-10 MPa, the weight hourly space velocity of methylal is 0.5-3.0 h$^{-1}$, the molar ratio of carbon monoxide to methylal is 2:1-15:1, and the preferred molar ratio of hydrogen gas to methylal is 1:1-3:1.

In one preferred embodiment, the process of the reaction is a gas-liquid-solid three-phase reaction, the reaction temperature is 60-90° C., the reaction pressure is 5-10 MPa, the weight hourly space velocity of methylal is 0.5-1.5 h$^{-1}$, the molar ratio of carbon monoxide to methylal is 2:1-10:1, and the preferred molar ratio of hydrogen gas to methylal is 1:1-2:1.

In some embodiments, both the conversion rate of methylal and the selectivity of the product are calculated based on moles of carbons of methylal:

Conversion rate of methylal=[(moles of carbons of methylal in feed)−(moles of carbons of methylal in discharge)]÷(moles of carbons of methylal in feed)×(100%)

Selectivity of methyl methoxyacetate=(moles of carbons of methyl methoxyacetate with carbonyl groups deducted in discharge)÷[(moles of carbons of methylal in feed)−(moles of carbons of methylal in discharge]×(100%)

Selectivity of polyoxymethylene dimethyl ether carbonyl compound=(moles of carbons of polyoxymethylene dimethyl ether carbonyl compound with carbonyl groups deducted in discharge)÷[(moles of carbons of methylal in feed)−(moles of carbons of methylal in discharge]×(100%)

The polyoxymethylene dimethyl ether carbonyl compound is a product having a structural unit of —O—(CO)—CH$_2$—O— or —O—CH$_2$—(CO)—O— formed by inserting a carbonyl group —CO— on a structural unit of —O—CH$_2$—O— of the molecular chain of polyoxymethylene dimethyl ether. The polyoxymethylene dimethyl ether carbonyl compound contains one or more carbonyl groups.

The polyoxymethylene dimethyl ether carbonyl compound generated in an embodiment may be one or more of CH$_3$—O—(CO)—CH$_2$—O—CH$_2$—O—CH$_3$, which is simply referred to as C5-1, CH$_3$—O—CH$_2$—(CO)—O—CH$_2$—O—CH$_3$, which is simply referred to as C5-2, CH$_3$—O—(CO)—CH$_2$—O—(CO)—CH$_2$—O—CH$_3$, which is simply referred to as C6-1, and CH$_3$—O—(CO)—CH$_2$—O—CH$_2$—(CO)—O—CH$_3$, which is simply referred to as C6-2.

The product: methyl methoxyacetate or polyoxymethylene dimethyl ether carbonyl compound of this invention may provide ethylene glycol by hydrolysis after hydrogenation or hydrogenation after hydrolysis. Moreover, the product may also be used as gasoline additives or diesel additives. For example, the process of reaction for generating ethylene glycol, which is briefly expressed by exemplifying dioxymethylene dimethyl ether (DMM$_2$) CH$_3$O(CH$_2$O)$_2$CH$_3$, is as follows:

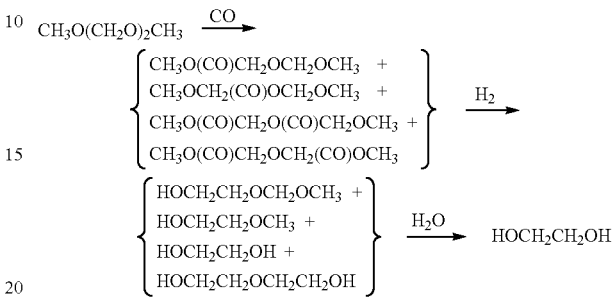

In one preferred embodiment, the reactor is a fixed bed reactor, a tank reactor, a moving bed reactor, or a fluidized bed reactor for continuously flows.

This present invention will be described in detail below by Examples, but this invention is not limited thereto.

Example 1

50 g of acidic MCM-22 molecular sieve catalyst with a silicon-to-aluminum ratio (Si:Al)=40:1 was baked under air atmosphere of a muffle furnace at 550° C. for 5 hours, and a powder sample as a part thereof was taken, tablet-compressed, and pulverized to 20-40 mesh for activity test. 10 g of this acidic MCM-22 molecular sieve catalyst sample was weighed and charged in a stainless reaction tube with an inner diameter of 8.5 mm, and was activated with nitrogen gas under normal pressure at 550° C. for 4 hours. The temperature was reduced to reaction temperature (T)=90° C., carbon monoxide:dioxymethylene dimethyl ether:hydrogen gas(CO:DMM$_2$:H$_2$)=7:1:1 was introduced, and the pressure was slowly increased to reaction pressure (P)=10 MPa, with the weight hourly space velocity (WHSV) of dioxymethylene dimethyl ether=0.2 h$^{-1}$. The product was analyzed by gas chromatography, and the conversion rate of dioxymethylene dimethyl ether and the selectivity of polyoxymethylene dimethyl ether carbonyl compound were calculated after the reaction is substantially stable. The results of the reaction can be seen in Table 1.

Example 2

The catalyst in Example 1 was changed to acidic ferrierite molecular sieve, wherein Si:Al=10:1, T=60° C., CO:DMM$_2$:H$_2$=13:1:3, P=4 MPa, and WHSV=1.5 h$^{-1}$, and the remaining experimental steps were consistent with those in Example 1. The results of the reaction can be seen in Table 1.

Example 3

The catalyst in Example 1 was changed to acidic ZSM-5 molecular sieve, wherein Si:Al=150:1, T=140° C., CO:DMM$_2$:H$_2$=2:1:5, P=6.5 MPa, and WHSV=3.0 h$^{-1}$, and the remaining experimental steps were consistent with those in Example 1. The results of the reaction can be seen in Table 1.

Example 4

The catalyst in Example 1 was changed to acidic zeolite mordenite molecular sieve, wherein Si:Al=3:1, T=105° C., CO:DMM$_2$:H$_2$=20:1:1, P=5.0 MPa, and WHSV=1.0 h$^{-1}$, and the remaining experimental steps were consistent with those in Example 1. The results of the reaction can be seen in Table 1.

Example 5

The catalyst in Example 1 was changed to acidic Y molecular sieve, wherein Si:Al=20:1, T=73° C., CO:DMM$_2$:H$_2$=10:1:2, P=2 MPa, and WHSV=10.0 h$^{-1}$, and the remaining experimental steps were consistent with those in Example 1. The results of the reaction can be seen in Table 1.

Example 6

The catalyst in Example 1 was changed to acidic Beta molecular sieve, wherein Si:Al=15:1, T=120° C., CO:DMM$_2$:H$_2$=15:1:4, P=4.7 MPa, and WHSV=0.5 h$^{-1}$, and the remaining experimental steps were consistent with those in Example 1. The results of the reaction can be seen in Table 1.

Example 7

50 g of acidic ZSM-5 molecular sieve catalyst with a silicon-to-aluminum ratio (Si:Al)=40:1 was baked under air atmosphere of a muffle furnace at 550° C. for 5 hours, and a powder sample as a part thereof was taken, tablet-compressed, and pulverized to 20-40 mesh for activity test. 10 g of this acidic ZSM-5 molecular sieve catalyst sample was weighed and charged in a stainless reaction tube with an inner diameter of 8.5 mm, and was activated with nitrogen gas under normal pressure at 550° C. for 4 hours. The temperature was reduced to reaction temperature (T)=88° C., raw materials in which carbon monoxide:dioxymethylene dimethyl ether:hydrogen gas(CO:DMM$_n$:H$_2$)=8:1:1 was introduced, wherein the mass ratio of respective components in DMM$_n$ is: $_2$:DMM$_3$:DMM$_4$:DMM$_5$:DMM$_6$=51.2:26.6: 12.8:6.5:2.9, and the pressure was slowly increased to reaction pressure (P)=8 MPa, with the weight hourly space velocity (WHSV) of dioxymethylene dimethyl ether=1.5 h$^{-1}$. The product was analyzed by gas chromatography. The results of the reaction can be seen in Table 1.

Example 8

50 g of acidic Y molecular sieve catalyst with a silicon-to-aluminum ratio (Si:Al)=23:1 was baked under air atmosphere of a muffle furnace at 550° C. for 5 hours, and a powder sample as a part thereof was taken, tablet-compressed, and pulverized to 20-40 mesh for activity test. 10 g of this acidic Y molecular sieve catalyst sample was weighed and charged in a stainless reaction tube with an inner diameter of 8.5 mm, and was activated with nitrogen gas under normal pressure at 550° C. for 4 hours. The temperature was reduced to reaction temperature (T)=95° C., raw materials in which carbon monoxide:dioxymethylene dimethyl ether:hydrogen gas(CO:DMM$_n$:H$_2$)=10:1:1 was introduced, wherein the mass ratio of respective components in DMM$_n$ is: $_2$:DMM$_3$:DMM$_4$:DMM$_5$:DMM$_6$=47.7:26.9:14.0: 7.8:3.6, and the pressure was slowly increased to reaction pressure (P)=7 MPa, with the weight hourly space velocity (WHSV) of dioxymethylene dimethyl ether=2.0 h$^{-1}$. The product was analyzed by gas chromatography. The results of the reaction can be seen in Table 1.

Comparative Example 1

The ratio of gases in Example 4 was changed to CO:DMM$_2$:H$_2$=20:1:0, and the remaining experimental steps were consistent with those in Example 4. The results of the reaction can be seen in Table 1.

Comparative Example 2

The ratio of gases in Example 5 was changed to CO:DMM$_2$:H$_2$=10:1:0, and the remaining experimental steps were consistent with those in Example 5. The results of the reaction can be seen in Table 1.

TABLE 1

Results of catalytic reactions in Examples 1-8 and Comparative Examples 1-2

| | Catalyst/ silicon-to-aluminum ratio | CO:DMM$_n$:H$_2$ | T, P, and WHSV | Conversion of DMM$_n$ (%) | Selectivities of C5-1, C5-2, C6-1, C6-2 (%) | Selectivity of polyoxymethylene dimethyl ether carbonyl compound (%) | Single-pass life of catalyst (days) |
|---|---|---|---|---|---|---|---|
| Example 1 | MCM-22/ 40:1 | 7:1:1 | 90° C., 10.0 MPa, 0.2 h$^{-1}$ | 85.0 | 35.3, 22.5, 16.2, 9.2 | 92.3 | 20 |
| Example 2 | Ferrierite/ 10:1 | 13:1:3 | 60° C., 4.0 MPa, 1.5 h$^{-1}$ | 83.9 | 36.2, 21.1, 14.2, 12.0 | 91.5 | 18 |
| Example 3 | ZSM-5/ 150:1 | 2:1:5 | 140° C., 6.5 MPa, 3.0 h$^{-1}$ | 91.7 | 37.4, 24.7, 16.1, 13.0 | 93.2 | 25 |
| Example 4 | Zeolite mordenite/3:1 | 20:1:1 | 105° C., 5.0 MPa, 1.0 h$^{-1}$ | 79.6 | 28.3, 22.2, 13.0, 9.0 | 86.4 | 15 |
| Example 5 | Y/ 20:1 | 10:1:2 | 73° C., 2.0 MPa, 10.0 h$^{-1}$ | 86.6 | 38.2, 24.0, 16.5, 13.8 | 94.1 | 32 |
| Example 6 | Beta/ 15:1 | 15:1:4 | 120° C., 4.7 MPa, 0.5 h$^{-1}$ | 82.1 | 28.9, 24.2, 17.1, 13.0 | 88.6 | 22 |
| Example 7 | ZSM-5/ 40:1 | 8:1:1 | 88° C., 8.0 MPa, 1.5 h$^{-1}$ | 75.2 | — | 87.5 | 21 |

TABLE 1-continued

Results of catalytic reactions in Examples 1-8 and Comparative Examples 1-2

| | Catalyst/ silicon-to-aluminum ratio | CO:DMM$_n$:H$_2$ | T, P, and WHSV | Conversion of DMM$_n$ (%) | Selectivities of C5-1, C5-2, C6-1, C6-2 (%) | Selectivity of polyoxymethylene dimethyl ether carbonyl compound (%) | Single-pass life of catalyst (days) |
|---|---|---|---|---|---|---|---|
| Example 8 | Y/ 23:1 | 10:1:1 | 95° C., 7.0 MPa, 2.0 h$^{-1}$ | 85.2 | — | 91.3 | 52 |
| Comparative Example 1 | Zeolite mordenite/3:1 | 20:1:0 | 105° C., 5.0 MPa, 1.0 h$^{-1}$ | 75.4 | 25.3, 20.2, 11.0, 9.0 | 83.2 | 11 |
| Comparative Example 2 | Y/ 20:1 | 10:1:0 | 73° C., 2.0 MPa, 10.0 h$^{-1}$ | 82.1 | 35.2, 22.0, 15.5, 13.5 | 90.1 | 25 |

Example 9

50 g of acidic MCM-22 molecular sieve catalyst with a silicon-to-aluminum ratio (Si:Al)=40:1 was baked under air atmosphere of a muffle furnace at 550° C. for 5 hours, and a powder sample as a part thereof was taken, tablet-compressed, and pulverized to 20-40 mesh for activity test. 10 g of this acidic MCM-22 molecular sieve catalyst sample was weighed and charged in a stainless reaction tube with an inner diameter of 8.5 mm, and was activated with nitrogen gas under normal pressure at 550° C. for 4 hours. The temperature was reduced to reaction temperature (T)=90° C., carbon monoxide:methylal:hydrogen gas(CO:DMM:H$_2$)=7:1:1 was introduced, and the pressure was slowly increased to reaction pressure (P)=10 MPa, with the weight hourly space velocity (WHSV) of methylal=0.2 h$^{-1}$. The product was analyzed by gas chromatography, and the conversion rate of methylal and the selectivity of the product were calculated after the reaction is stable. The results of the reaction can be seen in Table 2.

Example 10

The catalyst in Example 9 was changed to acidic ferrierite molecular sieve, wherein Si:Al=10:1, T=60° C., CO:DMM:H$_2$=13:1:3, P=4 MPa, and WHSV=1.5 h$^{-1}$, and the remaining experimental steps were consistent with those in Example 9. The results of the reaction can be seen in Table 2.

Example 11

The catalyst in Example 9 was changed to acidic ZSM-5 molecular sieve, wherein Si:Al=150:1, T=140° C., CO:DMM:H$_2$=2:1:5, P=6.5 MPa, and WHSV=3.0 h$^{-1}$, and the remaining experimental steps were consistent with those in Example 9. The results of the reaction can be seen in Table 2.

Example 12

The catalyst in Example 9 was changed to acidic zeolite mordenite molecular sieve, wherein Si:Al=3:1, T=105° C., CO:DMM:H$_2$=20:1:1, P=5.0 MPa, and WHSV=1.0 h$^{-1}$, and the remaining experimental steps were consistent with those in Example 9. The results of the reaction can be seen in Table 2.

Example 13

The catalyst in Example 9 was changed to acidic Y molecular sieve, wherein Si:Al=20:1, T=73° C., CO:DMM:H$_2$=10:1:2, P=2 MPa, and WHSV=10.0 h$^{-1}$, and the remaining experimental steps were consistent with those in Example 9. The results of the reaction can be seen in Table 2.

Example 14

The catalyst in Example 9 was changed to acidic Beta molecular sieve, wherein Si:Al=15:1, T=120° C., CO:DMM:H$_2$=15:1:4, P=4.7 MPa, and WHSV=0.5 h$^{-1}$, and the remaining experimental steps were consistent with those in Example 9. The results of the reaction can be seen in Table 2.

Comparative Example 3

The ratio of gases in Example 12 was changed to CO:DMM:H$_2$=20:1:0, and the remaining experimental steps were consistent with those in Example 12. The results of the reaction can be seen in Table 2.

Comparative Example 4

The ratio of gases in Example 13 was changed to CO:DMM:H$_2$=10:1:0, and the remaining experimental steps were consistent with those in Example 13. The results of the reaction can be seen in Table 2.

TABLE 2

Results of catalytic reactions in Examples 9-14

| | Catalyst/ silicon-to-aluminum ratio | CO:DMM:H$_2$ | T, P, and WHSV | Conversion rate of methylal (%) | Selectivity of methyl methoxyacetate (%) | Selectivities of C5-1, C5-2, C6-1, C6-2 (%) | Single-pass life of catalyst (day) |
|---|---|---|---|---|---|---|---|
| Example 9 | MCM-22/ 40:1 | 7:1:1 | 90° C., 10.0 MPa, 0.2 h$^{-1}$ | 65.4 | 75.6 | 8.5, 5.5, 3.5, 1.5 | 18 |
| Example 10 | Ferrierite/ 10:1 | 13:1:3 | 60° C., 4 MPa, 1.5 h$^{-1}$ | 73.4 | 72.0 | 8.2, 5.1, 4.2, 2.0 | 15 |

TABLE 2-continued

Results of catalytic reactions in Examples 9-14

| | Catalyst/ silicon-to-aluminum ratio | CO:DMM:H$_2$ | T, P, and WHSV | Conversion rate of methylal (%) | Selectivity of methyl methoxyacetate (%) | Selectivities of C5-1, C5-2, C6-1, C6-2 (%) | Single-pass life of catalyst (day) |
|---|---|---|---|---|---|---|---|
| Example 11 | ZSM-5/ 150:1 | 2:1:5 | 140° C., 6.5 MPa, 3.0 h$^{-1}$ | 62.9 | 77.1 | 7.7, 4.8, 4.1, 3.1 | 24 |
| Example 12 | Zeolite mordenite/3:1 | 20:1:1 | 105° C., 5.0 MPa, 1.0 h$^{-1}$ | 50.9 | 75.9 | 8.3, 5.2, 3.1, 2.0 | 12 |
| Example 13 | Y/ 20:1 | 10:1:2 | 73° C., 2.0 MPa, 10.0 h$^{-1}$ | 56.9 | 80.1 | 6.2, 4.0, 1.5, 0.8 | 30 |
| Example 14 | Beta/ 15:1 | 15:1:4 | 120° C., 4.7 MPa, 0.5 h$^{-1}$ | 73.3 | 69.8 | 8.9, 6.2, 3.1, 2.0 | 17 |
| Comparative Example 3 | Zeolite mordenite/3:1 | 20:1:0 | 105° C., 5.0 MPa, 1.0 h$^{-1}$ | 47.2 | 71.6 | 8.2, 4.2, 3.0, 1.8 | 10 |
| Comparative Example 4 | Y/ 20:1 | 10:1:0 | 73° C., 2.0 MPa, 10.0 h$^{-1}$ | 51.8 | 75.1 | 6.1, 3.5, 1.3, 0.7 | 24 |

The advantageous effects of this invention include but are not limited to: the catalyst used in the method of this invention is a molecular sieve and the raw material is a mixed gas of polyoxymethylene dimethyl ether or methylal with carbon monoxide and hydrogen gas. Under the reaction conditions of this invention, it is capable of stably and efficiently producing a polyoxymethylene dimethyl ether carbonyl compound or methyl methoxyacetate as an intermediate for producing ethylene glycol by passing raw materials through the catalyst, and the process of the reaction is a gas-liquid-solid three-phase reaction. The carbonylation reaction of polyoxymethylene dimethyl ether or methylal is a strongly exothermic reaction. In this invention, the reaction temperature is relatively low, and along with large heat capacity of liquid phase and latent heat of phase transition, the reaction temperature can be well controlled, and the problem of temperature runaway in the process of industrial production is prevented. At the same time, the gas-liquid-solid three-phase reaction used in this invention can be operated at a high concentration of polyoxymethylene dimethyl ether or methylal, which increases single-pass reaction throughput in industrial production, reduces energy consumption in the processes of compression, circulation, and separation, and improves economic performance.

In this invention, the conversion rate of the raw material of polyoxymethylene dimethyl ether or methylal is high, the selectivity of the product of polyoxymethylene dimethyl ether carbonyl compound or methyl methoxyacetate is high, and the single-pass life of the catalyst is long. Moreover, in the method of this invention, the raw material reactant or the product in liquid phase itself is a good solvent, and additional solvents are not required to be used. Furthermore, the reactant or the product in liquid phase may dissolve carbon-predeposited substances in the process of catalytic reaction, which may be favorable to the improvement of the activity and the stability of the catalyst. The method of this invention enables continuous production and has the potential for industrial application.

Also, in this invention, a mixed gas of carbon monoxide and hydrogen gas is used as gas phase in the carbonylation reaction. Compared to existing techniques for producing ethylene glycol in the coal chemical industry which requires high-purity carbon monoxide, this invention does not require high-purity carbon monoxide, and may greatly decrease energy consumption of synthesis gas separation and improve the economy in the process of production. In addition, by adding hydrogen gas to the reaction gas, it is possible to increase the conversion rate of polyoxymethylene dimethyl ether or methylal and the selectivity of polyoxymethylene dimethyl ether carbonyl compound or methyl methoxyacetate and elongate the single-pass life of the catalyst.

Moreover, the polyoxymethylene dimethyl ether carbonyl compound or methyl methoxyacetate produced in this invention may be used to produce ethylene glycol by hydrolysis after hydrogenation or hydrogenation after hydrolysis.

This invention has been described in detail above, but this invention is not limited to specific embodiments described herein. It is to be understood by the person skilled in the art that other modifications and variations can be made without departing from the scope of the invention. The scope of the invention is defined by the appended claims.

The invention claimed is:

1. A method for preparing a polyoxymethylene dimethyl ether carbonyl compound as an intermediate for producing ethylene glycol by carbonylation, wherein a raw material: polyoxymethylene dimethyl ether CH$_3$O(CH$_2$O)$_n$CH$_3$, together with carbon monoxide and hydrogen gas is passed through a reactor carrying an acidic molecular sieve catalyst, and a reaction is performed to prepare a product: a polyoxymethylene dimethyl ether carbonyl compound, under conditions wherein the reaction temperature is 60-140° C., the reaction pressure is 2-10 MPa, the weight hourly space velocity of polyoxymethylene dimethyl ether is 0.2-10.0 h$^{-1}$, and no other solvent is added, wherein under the condition of the reaction, at least one of the raw material and the product is liquid phase, the acidic molecular sieve catalyst is solid phase, and carbon monoxide and hydrogen gas are gas phase, such that the process of the reaction is a gas-liquid-solid three-phase reaction, and the molar ratio of carbon monoxide to the raw material is 2:1-20:1 and the molar ratio of hydrogen gas to the raw material is 1:1-5:1, wherein n≥2 and is an integer, wherein the acidic molecular sieve catalyst is selected from the group consisting of MCM-22 molecular sieve, ferrierite, ZSM-5 molecular sieve, Y zeolite, Beta molecular sieve, and combinations thereof, the reactor is a fixed bed reactor which facilitates continuous reaction.

2. A method for preparing methyl methoxyacetate and a polyoxymethylene dimethyl ether carbonyl compound as intermediates for producing ethylene glycol by carbonylation, wherein a raw material: methylal CH$_3$O—CH$_2$—OCH$_3$, together with carbon monoxide and hydrogen gas is passed through a reactor carrying an acidic molecular sieve catalyst, and a reaction is performed to prepare products:

methyl methoxyacetate and a polyoxymethylene dimethyl ether carbonyl compound under conditions wherein the reaction temperature is 60-140° C., the reaction pressure is 2-10 MPa, the weight hourly space velocity of methylal is 0.2-10.0 h$^{-1}$, and no other solvent is added, wherein under the condition of the reaction, at least one of the raw material and the product is liquid phase, the acidic molecular sieve catalyst is solid phase, and carbon monoxide and hydrogen gas are gas phase, such that the process of the reaction is a gas-liquid-solid three-phase reaction, and the molar ratio of carbon monoxide to the raw material is 2:1-20:1 and the molar ratio of hydrogen gas to the raw material is 1:1-5:1, wherein the acidic molecular sieve catalyst is selected from the group consisting of MCM-22 molecular sieve, ferrierite, ZSM-5 molecular sieve, Y zeolite, Beta molecular sieve, and combinations thereof, the reactor is a fixed bed reactor which facilitates continuous reaction.

3. The method according to claim 1, wherein the product: polyoxymethylene dimethyl ether carbonyl compound, is a product having a structural unit of —O—(CO)—CH$_2$—O— or —O—CH$_2$—(CO)—O— formed by inserting one or more carbonyl groups —CO— in a structural unit of —O—CH$_2$—O— of the molecular chain of polyoxymethylene dimethyl ether CH$_3$O(CH$_2$O)$_n$CH$_3$, wherein n≥2.

4. The method according to claim 1 wherein the polyoxymethylene dimethyl ether is dioxymethylene dimethyl ether CH$_3$O(CH$_2$O)$_2$CH$_3$.

5. The method according to claim 1, wherein the polyoxymethylene dimethyl ether carbonyl compound is one or more of

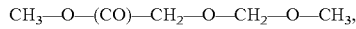

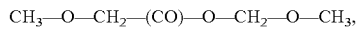

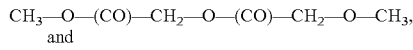
and

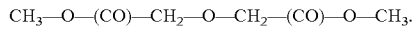

6. The method according to claim 1 wherein the reaction temperature is 60-120° C., the reaction pressure is 4-10 MPa, the weight hourly space velocity of the raw material is 0.5-3.0 h$^{-1}$, the molar ratio of carbon monoxide to the raw material is 2:1-15:1, and the molar ratio of hydrogen gas to the raw material is 1:1-3:1.

7. The method according to claim 1, wherein the reaction temperature is 60-90° C., the reaction pressure is 5-10 MPa, the weight hourly space velocity of the raw material is 0.5-1.5 h$^{-1}$, the molar ratio of carbon monoxide to the raw material is 2:1-10:1, and the molar ratio of hydrogen gas to the raw material is 1:1-2:1.

8. The method according to claim 2, wherein the product: polyoxymethylene dimethyl ether carbonyl compound, is a product having a structural unit of —O—(CO)—CH$_2$—O— or —O—CH$_2$—(CO)—O— formed by inserting one or more carbonyl groups —CO— in a structural unit of —O—CH$_2$—O— of the molecular chain of polyoxymethylene dimethyl ether CH$_3$O(CH$_2$O)$_n$CH$_3$, wherein n≥2.

9. The method according to claim 2, wherein the polyoxymethylene dimethyl ether carbonyl compound is one or more of

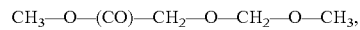

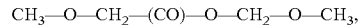

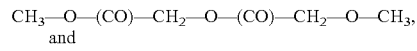
and

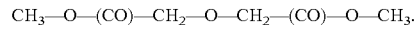

10. The method according to claim 2, wherein the reaction temperature is 60-120° C., the reaction pressure is 4-10 MPa, the weight hourly space velocity of the raw material is 0.5-3.0 h$^{-1}$, the molar ratio of carbon monoxide to the raw material is 2:1-15:1, and the molar ratio of hydrogen gas to the raw material is 1:1-3:1.

11. The method according to claim 2, wherein the reaction temperature is 60-90° C., the reaction pressure is 5-10 MPa, the weight hourly space velocity of the raw material is 0.5-1.5 h$^{-1}$, the molar ratio of carbon monoxide to the raw material is 2:1-10:1, and the molar ratio of hydrogen gas to the raw material is 1:1-2:1.

* * * * *